(12) United States Patent
Olson et al.

(10) Patent No.: US 6,836,733 B1
(45) Date of Patent: Dec. 28, 2004

(54) BIOLOGICAL SEQUENCE PATTERN PROBE

(75) Inventors: N. Eric Olson, Seattle, WA (US); Jeff Kozlowski, Seattle, WA (US)

(73) Assignee: Vizx Labs, LLC, Seattle, WA (US)

( * ) Notice: Subject to any disclaimer, the term of this patent is extended or adjusted under 35 U.S.C. 154(b) by 0 days.

(21) Appl. No.: 10/349,681

(22) Filed: Jan. 22, 2003

Related U.S. Application Data

(60) Provisional application No. 60/351,244, filed on Jan. 22, 2002.

(51) Int. Cl.[7] .............................................. G01N 31/00
(52) U.S. Cl. ......................................... 702/27; 702/20
(58) Field of Search .......................... 702/27, 70, 70.9; 435/6, 483, 7.1, 5; 536/23.1; 900/278; 514/12

(56) References Cited

U.S. PATENT DOCUMENTS 6,453,241 B1 * 9/2002 Bassett, Jr. et al. ............ 702/19
6,553,317 B1 * 4/2003 Lincoln et al. ................. 702/20
2003/0162176 A1 * 8/2003 Edwards et al. ................ 435/6

* cited by examiner

*Primary Examiner*—Xiuqin Sun
(74) *Attorney, Agent, or Firm*—LaRiviere, Grubman & Payne, LLP

(57) ABSTRACT

A method and apparatus for determining biological sequence sites of interest using client 1 server 3 computer architecture. In the method, one or more users (not shown) use computer client or client 1 to select a biological sequence database 5 of interest, and determines the search parameters 7 which control the specificity of results to be returned. The remote computer client 1 submits the search request 11 to a central computer server 3, which processes search request 11. Once server 3 has received request 14, the claimed method is undertaken by PatternProbe Express 16 and results are returned 18 to one or more remote client(s) 1. Once received, results are viewed 22 according to the previously selected search parameters 7.

5 Claims, 3 Drawing Sheets

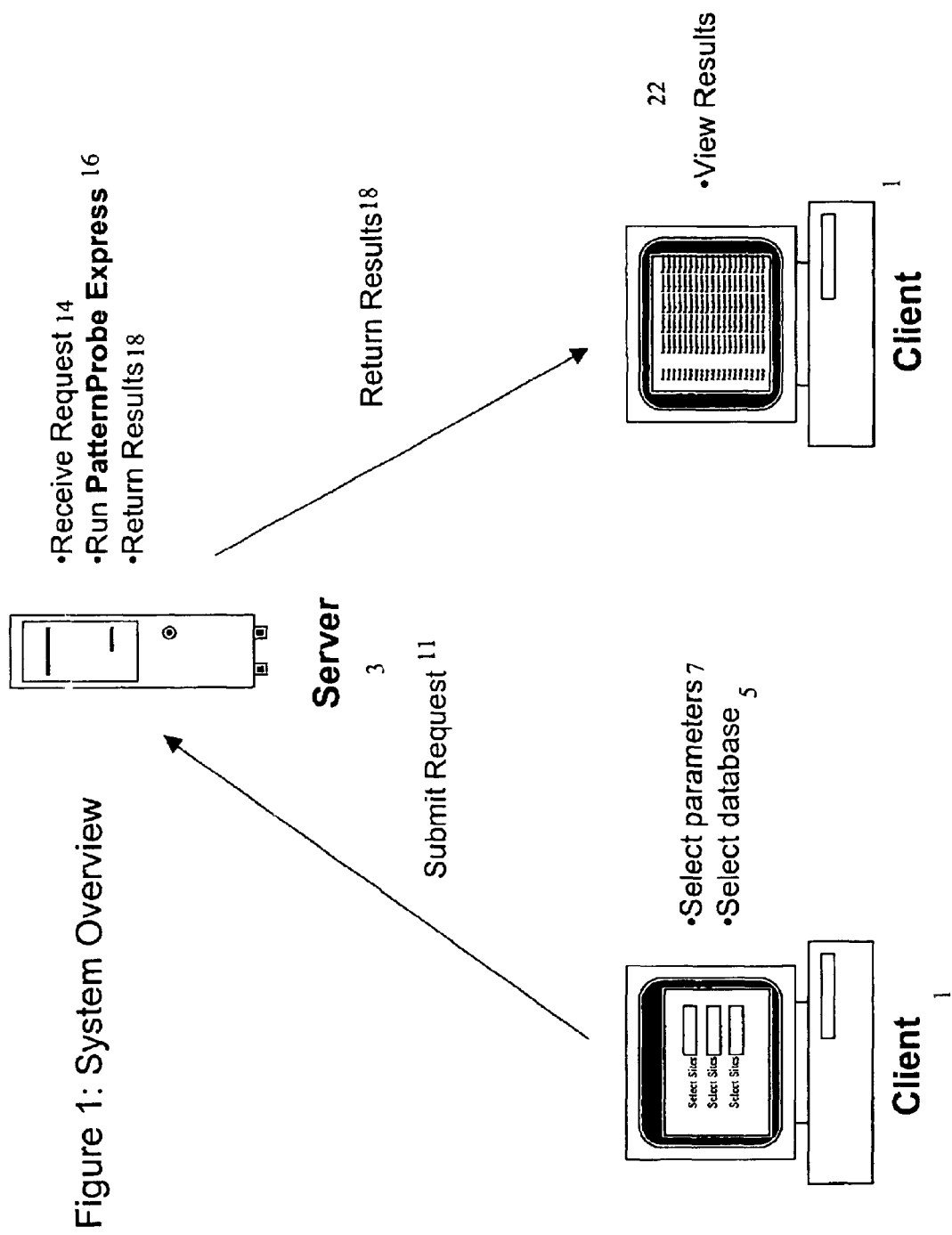
Figure 1: System Overview

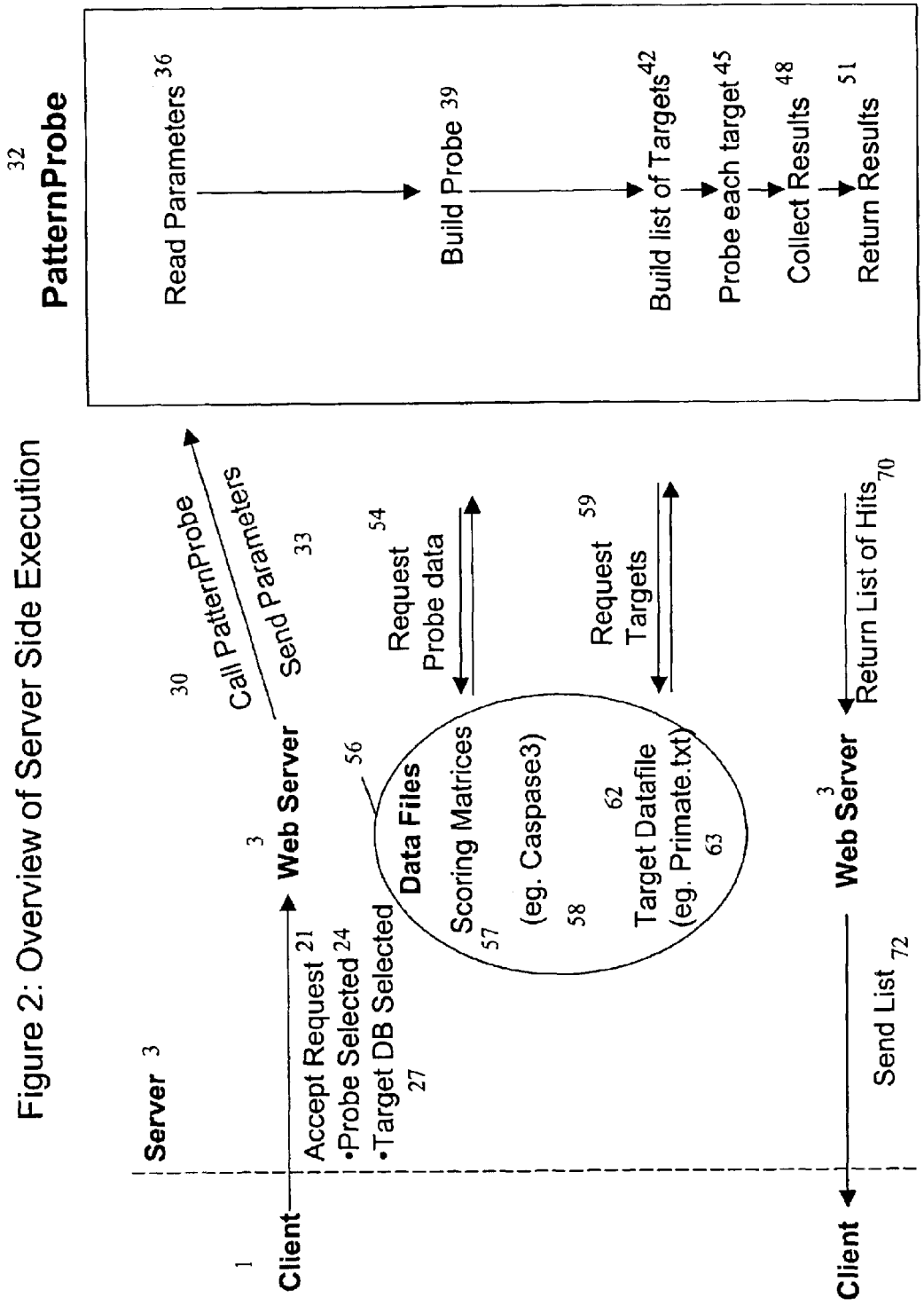
Figure 2: Overview of Server Side Execution

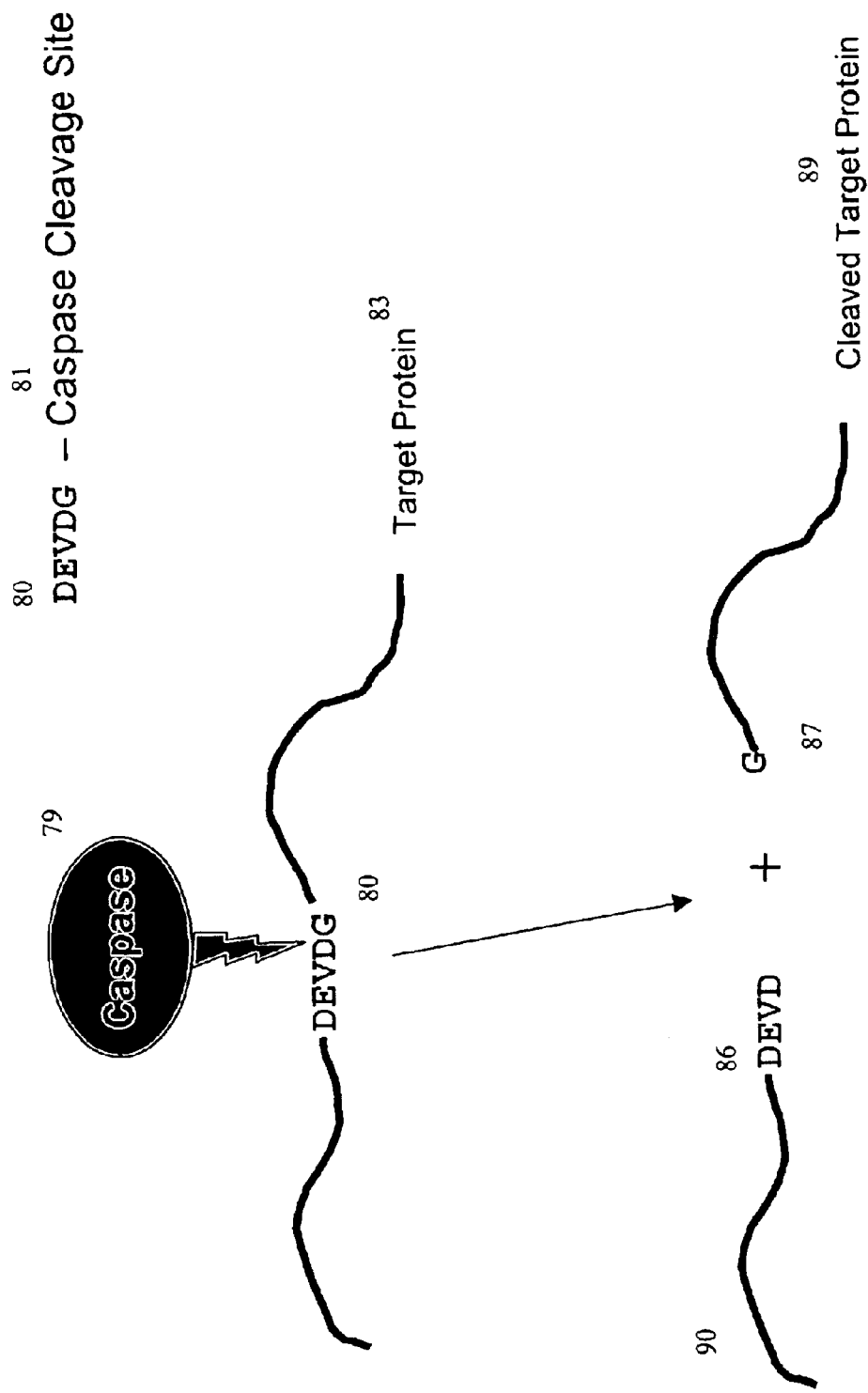

```
                          SEQUENCE LISTING

<160> NUMBER OF SEQ ID NOS: 1

<210> SEQ ID NO 1
<211> LENGTH: 5
<212> TYPE: PRT
<213> ORGANISM: Homo sapiens

<400> SEQUENCE: 1

Asp Glu Ala Asp Gly
1               5
```

BIOLOGICAL SEQUENCE PATTERN PROBE

RELATED APPLICATIONS

This application claims priority to U.S. Provisional Patent Application No. 60/351,244 filed on Jan. 22, 2002.

TECHNICAL FIELD

The present invention relates to the analysis of life science data. More particularly, the present invention relates to computer based interpretation of biological sequences. Even more particularly, the present invention relates to a client/server or Internet based computer tool and method for identification of potential protein, DNA or RNA sites of interest based upon the underlying amino acid or DNA or RNA nucleic acid sequence characteristics.

BACKGROUND ART

Currently, life scientists and molecular biologists are working with a wide variety of manual and automated tools to determine particular characteristics regarding molecular biology data. While automated protein sequencing tools presently generate large volumes of protein amino acid sequence data, tools for easily handling and interpreting the new data have yet to become commonplace. Scientists have been attempting to manage their molecular biology data in a wide variety of ways, from expensive, dedicated and proprietary computer systems to manually reviewing data placed into common word processors or text editors not optimized for handling large amounts of life science information.

The challenge of the first approach lies primarily in its limited accessibility by the average life scientist. Dedicated proprietary computer systems for sequencing and interpretation of molecular biology information often cost far beyond what the budgets of small research operations will permit. Other drawbacks exist in addition to acquisition price, such as closed and user unfriendly proprietary system architecture which does not facilitate cross-platform sharing of molecular biology sequence information. Often researchers using state of the art proprietary systems purchased at great expense will encounter difficulty sharing molecular biology data with other researchers on different computer systems in the same lab, let alone with colleagues in another institution or country.

The difficulty encountered at the other end of the spectrum is just as common, if not more so. Researchers not able to gain access to high cost dedicated molecular biology computer systems may resort to utilizing the most rudimentary of toolsets to interpret their genetic sequence or corresponding protein data. Manually screening through volumes of protein sequence data using basic text editors and word processors is not unheard of, despite the fact that these tools are not optimized for or never designed to handle genetic data in any form. In addition, despite the high degree of sophistication the average life scientist may have with respect to his or her particular field, often a commensurate computer ability is not present in the average life science user. User interfaces currently designed for state of the art molecular biology computer systems can be so user unfriendly that a life scientist may actually prefer to work with a simple and easy to use text editor instead of an inflexible proprietary system. As for the problem of collaborative work on related sequence data, neither approach facilitates remote access to lab generated or public domain sequence library information.

In the end, a technologically robust and user friendly system for remotely interpreting and managing life science data is truly needed. Such a system would aid not only the research process itself, but would speed the end product of the research as well. An improved and broadly accessible tool for interpreting life science data would not simply aid research in and of itself, but bring about discoveries in an accelerated manner. Data brought closer to understanding by the life scientist consequently means accelerated medical breakthroughs, improved drug therapies, and better understood systematic models of disease and regulatory processes.

DISCLOSURE OF INVENTION

By combining a powerful biological sequence site scoring tool with remote computer access functionality, a web-based tool for the identification of molecular biology sequence sites is hereby disclosed. An example of the present system and method functionality is provided using the identification of Caspase cleavage sites as a working example. Scoring as applied to potential protein modifications sites is based on amino acid sequence characterization, and is easily modifiable to be utilized by nucleic acid sequences.

Disclosed is an objective, quantitative method and apparatus for searching and evaluating biological sequence data relative to a selected functional characteristic, such as enzyme cleavage site, binding site, secondary structure, or potential modification site. Software is used to scan known target sequences of amino acids, DNA or RNA base pairs, searching for sequence regions exhibiting composition characteristics derived from scoring matrices provided by user input. Characteristics may include number of residues, presence of specific residues, or specific sequences of residues. Sequence regions exhibiting characteristics similar to the predetermined characteristics are identified, flagged and quantitatively scored for closeness of fit to the group of all predetermined characteristics, including quantitative scoring for mandatory characteristics and exclusionary characteristics. Scoring takes place based upon one or more scoring matrices which detail the individual predetermined characteristics and their respective quantitative scores. The scoring matrices can be used to predict the relative functional effect of individual biological sequences within a potential sequence site and help interpret combinations of sequences relative to the specific functional characteristic of interest. The invention further provides the user with the ability to select threshold cutoff values to be used by the software for evaluation of scoring matrix results, thereby assisting the user in the site location identification process, and providing the user the ability to evaluate the effect of substitutions of characteristics.

To practice the claimed invention on a particular protein amino acid sequence cleavage site, one or more scoring matrices are developed. These scoring matrices are derived by comparing the cleavage sites from known protein targets and determining the frequency of amino acid content at each position. A score for each possible amino acid is then set for each position based on this frequency. For example, a particular cleavage site in a protein may contain 5 amino acids. If it were found that Aspartic acid occurred 50% of the time at the first position and Leucine 50% of the time at this position, then each of these amino acids would have a score of 0.5 and the remaining amino acids would have a score of 0 at this position. To ensure the return of particular results, such as when particular amino acids must be present (weighted score greater than or equal to 1) or must not be present (negative weighted score), scores outside of the anticipated frequency range can also be inserted. Thus, for each of the five positions in a protein cleavage site a score for each of the 20 amino acids is created, this information is stored in the scoring matrix. Each possible cleavage site in a target protein is assigned a cumulative score based on this matrix. All possible cleavage sites can be listed, sorted by this score. A threshold can be set such that only scores above a certain level of identity are returned when queried. This search can be performed on a single protein or on large public protein databases, residing anywhere from the initial client computer, the central server computer, or remotely on public databases accessible via the Internet. The data searched can be resident on the server undertaking the analysis, or remotely retrieved from public or private sequence databases. In addition, the results returned can be sent to a single remote client computer, or to a plurality of remote systems. Due to the pervasive nature of the Internet, it is an intended consequence of the claimed invention that multi-user collaboration is made possible under the client/server computer model, with data sets and stored queries are easily shared among users.

In the working example of Caspases, the Caspases are a family of proteases that are known to play a key role in the regulation of programmed cell death (apoptosis). These proteins have a high degree of substrate specificity and Caspase cleavage of specific key regulatory proteins is thought to play an integral role in cell death. This specificity is achieved by recognition of specific amino acid patterns in target proteins, for example, the amino acid sequence DEADG (aspartic acid, glutamic acid, alanine, aspartic acid and glycine) in Retinoblastoma protein (pRb) is recognized and cleaved by Caspase 3 during apoptosis. The aspartic acid in the $4^{th}$ position is absolutely required for all Caspase cleavage, while the other 4 amino acids determine whether the sequence is cleaved by Caspases and if so by which Caspase. Thus, while aspartic acid residues are required for a Caspase cleavage site, the surrounding amino acids will determine whether Caspases can cleave the protein at that particular aspartic acid. Additionally, those surrounding amino acids can determine which Caspase acts on that site. Recently, it has become clear that Caspases can also regulate other cellular processes such as proliferation and differentiation. Thus, Caspases are critical regulators of cell fate and may play roles in the pathogenesis of diseases such as cancer, autoimmune disease, AIDS and Alzheimer's Disease. The identification of Caspase substrates may therefore provide insight into the regulatory pathways involved in these diseases, and advances in characterizing potential Caspase cleavage sites would clearly advance medical discoveries in these areas.

The claimed invention as applied to this working example scans a protein's amino acid sequence for potential cleavage sites and scores them using user-defined scoring matrices based on the consensus sites for several different proteases. In the working example of Caspases, the evaluated Caspase variants are Caspase 3, Caspase 6 and Caspase 8 respectively. These scoring matrices are derived by comparing the cleavage sites from known Caspase targets and determining the frequency of amino acid content at each position. A score for each possible amino acid is then set for each position based on this frequency. A score can also reflect particular user defined characteristics as well. For example, Caspase cleavage sites contain 5 amino acids. If it were found that Aspartic acid occurred 50% of the time at the first position and Leucine 50% of the time at this position, then each of these amino acids would have a score of 0.5 and the remaining amino acids would have a score of 0 at this position. For event determinative characteristics, a required amino acid at a particular position can be assigned a frequency score greater than one to guarantee inclusion of this indicator in the returned results. Also, amino acids requiring exclusion at a particular position can be assigned a score less than zero to ensure that potential sites including this amino acid at this position are not returned. Thus, for each of the five positions in a Caspase site a score for each of the 20 amino acids is created, this information is stored in the scoring matrix. Each possible cleavage site in a target protein is assigned a cumulative score based on this matrix. For Caspase cleavage, every aspartic acid is considered to be a potential cleavage site and is in fact required at the fourth sequence location, and is consequently assigned a value of '2' at the fourth position to guarantee inclusion in results returned. All possible cleavage sites can be listed, sorted by this score. A threshold can be set such that only scores above a certain level of identity are returned. This search can be performed on a single protein or on large public protein databases, located either on the client computer, central server computer, or remote public database accessible through the Internet. In the following tables, the exemplary scoring values for amino acids in Caspase cleavage sites are presented as Caspase 3, Caspase 6 and Caspase 8 tables, followed by the union table Caspaseall.

Table of Caspase 3 cleavage site scoring, length of site is 5, 4 is position of required amino acid D (Aspartic Acid)

| Amino Acid | 1st Position | 2nd Position | 3rd Position | 4th Position | 5th Position |
|---|---|---|---|---|---|
| A—Alanine | 0 | 0.032 | 0.048 | 0 | 1 |
| C—Cystine | 0 | −1 | −1 | 0 | 0 |
| D—Aspartic Acid | 1 | 0.016 | 0.016 | 2 | 0 |
| E—Glutamic Acid | 0 | 0.397 | 0.016 | 0 | 0 |
| F—Phenylalanine | 0 | −1 | −1 | 0 | 0 |
| G—Glycine | −1 | 0.048 | 0.032 | 0 | 1 |
| H—Histidine | 0 | 0.032 | 0.016 | 0 | 0 |
| I—Isoleucine | 0 | 0.048 | 0.016 | 0 | 0 |
| K—Lysine | −1 | −1 | −1 | 0 | 0 |
| L—Leucine | 0 | 0.095 | 0.095 | 0 | 0 |
| M—Methionine | 0 | 0.048 | 0.016 | 0 | 0 |
| N—Asparagine | 0 | −1 | 0.032 | 0 | 0 |
| P—Proline | 0 | 0.016 | 0.159 | 0 | 0 |
| Q—Glutamine | 0 | 0.048 | 0.063 | 0 | 0 |
| R—Arginine | −1 | 0.032 | −1 | 0 | 0 |
| S—Serine | 0 | 0.095 | 0.032 | 0 | 1 |
| T—Threonine | 0 | 0.032 | 0.159 | 0 | 0 |

-continued

| Amino Acid | 1st Position | 2nd Position | 3rd Position | 4th Position | 5th Position |
|---|---|---|---|---|---|
| V—Valine | 0 | 0.048 | 0.270 | 0 | 0 |
| W—Tryptophan | 0 | 0.016 | 0.016 | 0 | 0 |
| Y—Tyrosine | 0 | −1 | 0.016 | 0 | 0 |

Table of Caspase 6 cleavage site scoring, length of site is 5, 4 is position of required amino acid D (Aspartic Acid)

| Amino Acid | 1st Position | 2nd Position | 3rd Position | 4th Position | 5th Position |
|---|---|---|---|---|---|
| A—Alanine | 0 | 0.032 | 0.048 | 0 | 1 |
| C—Cystine | 0 | −1 | −1 | 0 | 0 |
| D—Aspartic Acid | 0 | 0.016 | 0.016 | 2 | 0 |
| E—Glutamic Acid | 0 | 0.397 | 0.016 | 0 | 0 |
| F—Phenylalanine | 0 | −1 | −1 | 0 | 0 |
| G—Glycine | −1 | 0.048 | 0.032 | 0 | 1 |
| H—Histidine | 0 | 0.032 | 0.016 | 0 | 0 |
| I—Isoleucine | 0 | 0.048 | 0.016 | 0 | 0 |
| K—Lysine | −1 | −1 | −1 | 0 | 0 |
| L—Leucine | 0.5 | 0.095 | 0.095 | 0 | 0 |
| M—Methionine | 0 | 0.048 | 0.016 | 0 | 0 |
| N—Asparagine | 0 | −1 | 0.032 | 0 | 0 |
| P—Proline | 0 | 0.016 | 0.159 | 0 | 0 |
| Q—Glutamine | 0 | 0.048 | 0.063 | 0 | 0 |
| R—Arginine | −1 | 0.032 | −1 | 0 | 0 |
| S—Serine | 0 | 0.095 | 0.032 | 0 | 1 |
| T—Threonine | 1 | 0.032 | 0.159 | 0 | 0 |
| V—Valine | 1 | 0.048 | 0.270 | 0 | 0 |
| W—Tryptophan | 0 | 0.016 | 0.016 | 0 | 0 |
| Y—Tyrosine | 0 | −1 | 0.016 | 0 | 0 |

Table of Caspase 8 cleavage site scoring, length of site is 5, 4 is position of required amino acid D (Aspartic Acid)

| Amino Acid | 1st Position | 2nd Position | 3rd Position | 4th Position | 5th Position |
|---|---|---|---|---|---|
| A—Alanine | 0 | 0.032 | 0.048 | 0 | 1 |
| C—Cystine | 0 | −1 | −1 | 0 | 0 |
| D—Aspartic Acid | 0.25 | 0.016 | 0.016 | 2 | 0 |
| E—Glutamic Acid | 0 | 0.397 | 0.016 | 0 | 0 |
| F—Phenylalanine | 0 | −1 | −1 | 0 | 0 |
| G—Glycine | −1 | 0.048 | 0.032 | 0 | 1 |
| H—Histidine | 0 | 0.032 | 0.016 | 0 | 0 |
| I—Isoleucine | 0 | 0.048 | 0.016 | 0 | 0 |
| K—Lysine | −1 | −1 | −1 | 0 | 0 |
| L—Leucine | 1 | 0.095 | 0.095 | 0 | 0 |
| M—Methionine | 0 | 0.048 | 0.016 | 0 | 0 |
| N—Asparagine | 0 | −1 | 0.032 | 0 | 0 |
| P—Proline | 0 | 0.016 | 0.159 | 0 | 0 |
| Q—Glutamine | 0 | 0.048 | 0.063 | 0 | 0 |
| R—Arginine | −1 | 0.032 | −1 | 0 | 0 |
| S—Serine | 0 | 0.095 | 0.032 | 0 | 1 |
| T—Threonine | 0 | 0.032 | 0.159 | 0 | 0 |
| V—Valine | 0.25 | 0.048 | 0.270 | 0 | 0 |
| W—Tryptophan | 0 | 0.016 | 0.016 | 0 | 0 |
| Y—Tyrosine | 0 | −1 | 0.016 | 0 | 0 |

Table of Caspaseall cleavage site scoring, length of site is 5, 4 is position of required amino acid D (Aspartic Acid)

| Amino Acid | 1st Position | 2nd Position | 3rd Position | 4th Position | 5th Position |
|---|---|---|---|---|---|
| A—Alanine | 0 | 0.032 | 0.048 | 0 | 1 |
| C—Cystine | 0 | −1 | −1 | 0 | 0 |
| D—Aspartic Acid | 1 | 0.016 | 0.016 | 2 | 0 |
| E—Glutamic Acid | 0 | 0.397 | 0.016 | 0 | 0 |
| F—Phenylalanine | 0 | −1 | −1 | 0 | 0 |
| G—Glycine | −1 | 0.048 | 0.032 | 0 | 1 |
| H—Histidine | 0 | 0.032 | 0.016 | 0 | 0 |
| I—Isoleucine | 0 | 0.048 | 0.016 | 0 | 0 |
| K—Lysine | −1 | −1 | −1 | 0 | 0 |
| L—Leucine | 1 | 0.095 | 0.095 | 0 | 0 |
| M—Methionine | 0 | 0.048 | 0.016 | 0 | 0 |
| N—Asparagine | 0 | −1 | 0.032 | 0 | 0 |
| P—Proline | 0 | 0.016 | 0.159 | 0 | 0 |
| Q—Glutamine | 0 | 0.048 | 0.063 | 0 | 0 |
| R—Arginine | −1 | 0.032 | −1 | 0 | 0 |
| S—Serine | 0 | 0.095 | 0.032 | 0 | 1 |
| T—Threonine | 1 | 0.032 | 0.159 | 0 | 0 |
| V—Valine | 1 | 0.048 | 0.270 | 0 | 0 |
| W—Tryptophan | 0 | 0.016 | 0.016 | 0 | 0 |
| Y—Tyrosine | 0 | −1 | 0.016 | 0 | 0 |

Summary of cleavage table and explanation. Once the scoring matrices have been developed (examples provided as Tables 1–4 above), sequence analysis can take place. In reviewing a particular protein sequence through the working model of potential Caspase cleavage sites, the presence of Aspartic acid at the fourth position is required. Consequently, in each of the detailed scoring tables, a value higher than one (2 in this working example) is assigned to Aspartic acid at the fourth position to account for its mandatory inclusion in any returned sequence. In addition, mandatory sequence information can be placed in a header to a given matrix which describes the length of the site followed by the location of the required amino acid. This would be '5 4' according to the Caspase working example, since the cleavage site is five amino acids long, with the required amino acid at the fourth position. A consequence of Caspase cleavage sites requiring an Aspartic acid at the fourth position is that sequence scoring may be optimized based upon this characteristic. While this optimization characteristic is clearly available when searching for Caspase cleavage sites, the presence of an absolutely required sequence can be used to similarly optimize sequence searches according to the following method. Since the Aspartic acid is required for a cleavage site, there is little benefit to scoring sequence data until an Aspartic acid is found. Since it is clearly easier for a computer to scan for a particular amino acid instead of reading sets of five amino acids and performing scoring calculations based upon a selected matrix, the present embodiment of the claimed invention reads through the sequences until an Aspartic acid is found. Scoring only then takes place based upon the sequences surrounding the Aspartic acid. Since Aspartic acid is required for the fourth sequence position in the cleavage site, scoring then takes place on the three amino acids prior to the Aspartic acid, as well as on the amino acid after the Aspartic acid. Throughput is thus optimized above and beyond that which would have been obtained if each and every amino acid in a protein had been scored.

In parallel with or subsequent to development of the scoring matrices, the threshold for returning results must be decided upon. This cutoff threshold will determine the specificity of potential characterization sites which will be returned. In the Caspase model, a threshold value of 4 was selected. This means that sequences scored with a particular matrix must have a value of greater than four to be returned in a search as a putative Caspase cleavage site. Applying the Caspase 3 scoring table to the known Caspase cleavage site of DEVDG listed in FIG. 3, this site would return a score of 4.667, which is well above the threshold cutoff value, and is in fact the highest score possible according to this scoring table. The value of 4.667 was arrived at based upon adding 1 for Aspartic Acid (which is required for Caspase 3 cleavage, hence the score of 1) at the first position added with 0.397 for Glutamic Acid at the second position added with 0.270 for Valine at the third position added with 2 for Aspartic Acid at the fourth position (the required amino acid in this example) added with 1 for Glycine at the fifth position (which is one of three possible required amino acids at this position). If a particular amino acid sequence did not have Aspartic Acid at the fourth position, the score would drop by two, since all other amino acids have a score of zero at the fourth position and would fall below the threshold cutoff score of four and not be returned. Similarly, if a particular amino acid sequence was expressly not desired at a particular sequence position, assigning that amino acid a negative score such as negative one would similarly select against a result containing that amino acid at the specified position. In the working example described, substituting phenylalanine for valine at the third position would drop the score by 1.270, since the value contributed by having valine at the third position would not be added, and phenylalanine has a score of negative one for the third position. Consequently, the five sequence value would become 3.397 and would be excluded as a potential Caspase 3 cleavage site since it is less than the threshold cutoff value of 4.

For the web-based implementation of the described tool and method, a programming language such as the Perl programming language may be used, in conjunction with Apache (open source web server software) and MySQL (an open source relational database) running under the Linux operating system. Key components can be implemented using a module written in the C programming language. Obviously, this tool and method can easily be extended to search for any user-defined protein motif in a protein. For example, to search for potential phosphorylation sites, a scoring matrix reflecting a user-defined phosphorylation consensus sequence would be substituted for the Caspase cleavage specific scoring matrixes used in the example presented. Minor modifications to the user interface would allow the user to select from all matrices available (e.g. Pull down menu). Similarly, other public or private protein databases could be substituted or added to those shown. Though protein databases are used in this example, the method could be extended to nucleotide databases provided these nucleotide sequences were translated into the appropriate amino acid sequence using a standard codon table prior to application of this method.

BRIEF DESCRIPTION OF THE DRAWINGS

FIG. 1 is a System Overview of the claimed invention

FIG. 2 is an Overview of the Server Side Execution

FIG. 3 is a diagram of Caspase Cleavage of Target Protein

MODES FOR CARRYING OUT THE INVENTION

FIG. 1 is a System Overview of the claimed invention. In utilizing the claimed methods to determine biological sequence sites of interest, a user (not shown) uses computer client 1 to select a biological sequence database 5 of interest, and determines the search parameters 7 which control characteristics such as the type of sequence site to be searched for and the specificity of results to be returned. The remote computer client 1 submits the search request 11 over a network such as the Internet to a central computer server 3, which processes search request 11. Once server 3 has received request 14 containing the sequence site to be characterized, the database to be queried and the specificity of results to be returned, the claimed method is undertaken by PatternProbe Express 16 and results are returned 18 to the remote client 1, or alternately to more than one remote client 1. Once received, results are viewed 22 according to the previously selected search parameters 7.

FIG. 2 is an Overview of the Server Side Execution. This figure is an overview of the claimed method from the perspective of the computer server based architecture. Once a request has been placed by client computer 1, the server computer 3 undertakes a number of steps to process and respond to a request. Once server 3 has accepted a request 21, a selection step for the desired probe 24 takes place, as well as selection of the target database 27. After selection, the web server 3 then calls 30 the PatternProbe 32 routine, passing parameters 33 to PatternProbe 32.

Once called, PatternProbe 32 first step is to read parameters 36, followed by building probe 39, building list of targets 42, probing each target 45, collecting results 48 and returning results 51. PatternProbe 32 interacts with data files 56 when requesting probe data 54 to retrieve scoring matrices 57 such as the Caspase3 scoring matrix 58 utilized in the working example. PatternProbe32 also interacts with data files 56 when requesting target data 59 by calling the target datafile 62, such as primate.txt datafile 63 as used in the working example.

After PatternProbe 32 has completed the return results 51 step, the step of returning list of hits 70 to the web server 3 is performed, so that web server 3 can send results list 72 to the client computer 1.

FIG. 3 is a diagram of Caspase Cleavage of Target Protein. Representative diagram of known in the art protein 83 cleavage by a Caspase 79. Target protein 83 is bound to by Caspase 79 at the caspase cleavage site 81, in this instance characterized by the amino acid sequence DEVDG 80. Once target protein 83 has been cleaved by caspase 79 at the caspase cleavage site 81, the cleaved caspase cleavage site results in two target protein halves 89 and 90 with corresponding cleaved cleavage site halves DEVD 86 and G 87 respectively.

Having illustrated and described the principles of the system and method of the present invention in various embodiments, it should be apparent to those skilled in the art that the embodiment can be modified in arrangement and detail without departing from such principles. For example, the biological sequences probed can be DNA base pairs instead of amino acids if preferred. Therefore, the illustrated embodiments should be considered only as example of the invention and not as a limitation on its scope. Although the description above contains much specificity, these should not be construed as limiting the scope of the invention but as merely providing illustrations of some of the presently preferred embodiments of this invention. Further, it is appreciated that the scope of the present invention encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention for it to be encompassed by the present claims. Furthermore, no element, component, or method step in the present disclosure is intended to be dedicated to the public regardless of whether the element, component, or method step is explicitly recited in the claim. No claim element herein is to be construed under the provisions of 35 U.S.C. 112, sixth paragraph, unless the clement is expressly recited using the phrase "means for".

INDUSTRIAL APPLICABILITY

The aforementioned invention has industrial applicability in the life science and molecular biology fields.

Sequence Listing

Sequence One: DEADG

Sequence Listing Free Text

```
Asp Glu Ala Asp Gly
1               5
```

Computer Code Listing

Please see enclosed Appendix A CD-Rom.

What is claimed is:

1. A method for identification and quantitative characterization of sequence sites of potential interest from one or more complex organic molecules, comprising the steps of:
   selecting one or more desired target sequence listings for analysis,
   scanning via computer said one or more target sequences for potential characterization sites,
   scoring said potential characterization sites using user-defined scoring matrices,
   deriving by comparing the sequence sites of interest from known sequence targets,
   determining the frequency of sequence content at each sequence position, and
   scoring for each possible amino acid or nucleic acid base pair sequences at each position based on said sequence content frequency,
   sorting said potential characterization sites according to predetermined scoring characteristics,
   returning results based upon said sorting, and
   listing said potential characterization sites within said one or more target sequences,
   said one or more target sequence listings code for data selected from the group comprising protein amino acid polypeptides, DNA nucleotide, and RNA nucleotide sequence listings.

2. The method of claim 1 wherein said scoring for each possible amino acid or nucleic acid base pair further comprises a pre-scoring step which reviews said amino acid or nucleic acid base pair sequences but does not score said sequences until a mandatory sequence as determined by said scoring matrices is encountered.

3. The method of claim 1 wherein said scoring for each possible amino acid or nucleic acid base pair additionally comprises assigning negative or highly positive score values to one or more amino acids or nucleic acid base pairs to make results deliberately returning or deliberately excluding said one or more amino acids or nucleic acid base pairs mandatory.

4. A distributed, collaborative computer apparatus for identification and quantitative characterization of potential characterization sites on a series of biological sequence data, comprising the elements of:
   a selection means for selecting one or more desired target biological sequences listing for analysis via one or more client computers,
   a creating means for creating one or more biological sequence characterization site matrices corresponding to said biological sequence type,
   a computer server scanning means for scanning via a server computer said target one or more biological sequences for potential characterization sites,
   a computer scoring means for scoring said potential characterization sites using user-defined scoring matrices,
   a computer sorting means for sorting said potential characterization sites according to predetermined scoring characteristics, an optimized means for scoring wherein biological sequence review occurs but scoring said potential characterization sites does not take place until a mandatory sequence required by said user-defined scoring matrices is encountered,
   a computer screening means for screening said potential characterization sites wherein the specificity of said results to be listed is user determined,
   a returning means for returning results to one or more client computer users based upon said sorting, and
   a listing means for listing said potential characterization sites within said target biological sequence.

5. A method for identification and quantitative characterization of potential characterization sites on a series of biological sequence data, comprising the steps of:
   selecting one or more desired target biological sequences listing for analysis via one or more client computers,
   creating one or more biological sequence characterization site matrices corresponding to said biological sequence type,
   scanning via a server computer said target one or more nucleic acid sequences for potential characterization sites,
   scoring said potential characterization sites using user-defined scoring matrices,
   sorting said potential characterization sites according to predetermined scoring characteristics,
   screening said potential characterization sites wherein the specificity of said results to be listed is user determined,
   returning results based upon said sorting
   listing said potential characterization sites within said target biological sequence,
   deriving said matrices by comparing the sites of interest from known sequence targets,
   determining the frequency of sequence content at each sequence position,
   scoring for each possible amino acid or DNA base pair at each position based on said sequence content frequency, and
   detailing in said matrices said scoring results.

* * * * *